United States Patent [19]

Navato

[11] Patent Number: 4,505,701
[45] Date of Patent: Mar. 19, 1985

[54] AUTOMATIC PARENTERAL INFUSION APPARATUS

[76] Inventor: Jose R. Navato, 3624 Blue Jacket Dr., Lee's Summit, Mo. 64063

[21] Appl. No.: 378,628

[22] Filed: May 17, 1982

[51] Int. Cl.³ .............................................. A61M 5/00
[52] U.S. Cl. ............................. 604/143; 128/DIG. 12
[58] Field of Search ............... 604/131, 141, 143, 146, 604/152, 154, 207, 208, 218, 219, 226, 228, 246, 249, 251, 135, 136; 128/DIG. 12

[56] References Cited

U.S. PATENT DOCUMENTS

| | | | |
|---|---|---|---|
| 2,545,017 | 3/1951 | Billingsley | 604/143 |
| 3,468,308 | 9/1969 | Bierman | 604/141 |
| 3,543,753 | 12/1970 | Weinstein | 604/141 |
| 3,604,417 | 9/1971 | Stolzenberg | 604/143 X |
| 3,605,745 | 9/1971 | Hodosh | 604/143 |

*Primary Examiner*—Stephen C. Pellegrino
*Attorney, Agent, or Firm*—Kokjer, Kircher, Bradley, Wharton, Bowman & Johnson

[57] ABSTRACT

Automatic parenteral infusion equipment for safely delivering, under substantially constant pressure and at a substantially constant rate of flow, infusion liquid to a patient's body. The apparatus includes a chamber for containing the infusion liquid, a pressure force remote from the infusion liquid chamber, a force transmission means interposed between the pressure source and the infusion liquid chamber, vent means to discharge compressible or incompressible fluid used as a force transmission vehicle in order to prevent the possibility of embolism or toxicity to the patient, and flow regulating member including a restricted orifice to deliver infusion liquid to the patient at a substantially constant rate. Alternative embodiments of the invention are disclosed for adaptation to both ambulatory and immobile patients.

7 Claims, 10 Drawing Figures

AUTOMATIC PARENTERAL INFUSION APPARATUS

BACKGROUND OF THE INVENTION

This invention relates to apparatus for automatic parenteral infusion of a liquid. More particularly, the invention relates to infusion apparatus in which the liquid to be infused into a patient is supplied at a relatively constant pressure to provide a constant, predetermined rate of infusion.

In the medical field, there is frequent need to introduce various liquids into the patient's body. Two techniques are commonly practiced but each suffer drawbacks under varying circumstances.

First, the liquid may be loaded into a conventional syringe and administered to the patient as a single injection through a hypodermic needle. As one example, diabetics may be supplied insulin using this technique. Medical science has determined, however, that it is frequently beneficial in health care to administer various medicinal liquids not at one time in a single dose, but at a slow rate over a prolonged period of time.

Such recognition gave rise to the second widely practiced technique for introducing liquids to a patient. Liquids such as saline solutions, plasma, whole blood and the like may be administered to a patient by inserting a needle into the patient's body and hanging a bottle or bag of the solution above the level of the patient so that the liquid is infused into the patient under positive pressure via flexible tubing connecting the bottle or bag and the needle. These parenteral liquid containers are typically elevated two to three feet above the patient and may be supported from a pole fastened to the patient's bed. This technique suffers from the obvious disadvantage that the patient's mobility is limited.

Oftentimes in the emergency treatment of trauma patients, intravenous solutions, for example, must be administered at the accident scene or while the patient is in route to medical facilities. Under these circumstances, the requirement of having an elevated intravenous container above the patient often presents difficulties because there is no provision for hanging the container. Thus, medical personnel must accompany the patient in order to hold the intravenous container at an appropriate, elevated position. In ambulances, helicopters, and similar medical evacuation vehicles, it may be difficult to properly position the intravenous bottle. Variations in height of the intravenous bottle above the patient will affect the pressure head of liquid and thus vary the flow rate of the solution to the patient.

To overcome the requirement of having to elevate an intravenous (IV) bottle, various apparatus have been proposed in which a flexible IV bag is pressurized either by gas pressure or by mechanical force. However, as the IV solution drains from the IV bag, the pressure force exerted on the bag also decreases thus lowering the pressure on the IV solution. This is the same problem encountered in varying the height of the bottle above the patient. To overcome this changing pressure problem, some of the known pressurized IV apparatus have a squeeze bulb which must be manually operated to increase the pressure on the IV bag as the IV solution empties therefrom. In other known pressurized IV apparatus, compressed gas from a source of compressed gas is regulated by means of a pressure regulator to maintain contant pressure on the IV bag. However, the requirement of a compressed gas source and a regulator appreciably increases the cost and complexity of the IV apparatus and, thence, the possibility of malfunction is increased.

The foregoing teachings of the prior art are embraced in the following patents.

U.S. Pat. No. 2,842,123 of Rundhaug, issued July 8, 1958 and entitled "Pressurized Tranfusion Apparatus", discloses a pressurized tranfusion apparatus having a sealed pressure container connected to a compressed gas source and having a collapsible tranfusion bag within the pressure container whereby the gas pressure acts directly on the bag to pressurize the liquid therein and to force delivery to the patient.

U.S. Pat. No. 3,153,414 by Beall et al, issued Oct. 20, 1964 and entitled "Apparatus for the Induced Infusion of Liquid from a Flexible Liquid Container", discloses infusion equipment in which an inflatable bladder encircles an intravenous liquid bag. The bladder is inflatable by a manually operated inflation squeeze bulb and exerts pressure on the intravenous bag to force fluid to the patient.

U.S. Pat. No. 3,468,308 of Bierman, issued Sept. 23, 1969 and entitled "Pressure Infusion Device for Ambulatory Patients with Pressure Control Means", teaches a collapsible bag contained within a rigid pressure shell equipped with a pressure regulating device to insure constant pressure and thus control delivery rate of intravenous liquid.

U.S. Pat. No. 3,507,278 of Werding, issued April 21, 1970 and entitled "Apparatus for Dispensing Parenteral Fluid", teaches transfusion apparatus in which a bag of liquid to be administered is contained within a rigid sealed vessel and is pressurized by gas pressure within the sealed vessel from a remote compressed gas source.

U.S. Pat. No. 3,838,794 by Cogley et al, issued Oct. 1, 1974 and entitled "Package for Storing and Dispensing Liquids", teaches a collapsible IV bag contained within a pressurized bladder connected to a regulated source of compressed air.

The teachings of the prior art, as exemplified by the foregoing references, have not been widely accepted in the medical field. As previously mentioned, gas regulating equipment adds to the cost and complexity of infusion apparatus of this genre. Medical personnel must be trained for the specific type of equipment being used and must be mindful of the varying techniques for regulating pressure on the IV solution. In spite of these significant drawbacks, however, an even more important problem exists in this equipment. It is, in fact, a potential health hazard. In the case of pressurized IV bags, the known prior art teaches pressurizing gas acting directly on the IV bag. In the event of a rupture of the IV bag, the pressurizing gas may enter the IV bag and ultimately be transmitted to the patient. The danger of air embolism is therefore thought to be the primary reason pressurized intravenous delivery equipment has not been widely utilized. Furthermore, a pressurizing gas desirable for its physical properties may be physiologically toxic if accidentally introduced to a patient due to equipment malfunction.

SUMMARY OF THE INVENTION

Accordingly, a need remains in the medical field for automatic parenteral infusion apparatus which is safe and which overcomes the drawbacks heretofore experienced with similar equipment in this art. The primary goal of this invention is to meet this need.

More particularly, an object of the invention is to provide pressurized, automatic parenteral infusion equipment which delivers parenteral solution at a predetermined and substantially constant rate and which includes features preventing the danger of toxicity or air embolism to the patient.

Yet another object of the invention is to provide automatic parenteral infusion equipment for administering parenteral solution which does not require the equipment to be elevated above the level of the person. Thus, the equipment is particularly useful in the field of emergency medical treatment.

A further object of the invention is to provide automatic infusion equipment of the character described which administers parenteral solution at a substantially constant regulated flow regardless of the amount of parenteral solution in the supply source. Thus eliminated is the need of continuous regulation and monitoring of the equipment by medical personnel. As a corollary advantage, the equipment is easily utilized by medical personnel accustomed to administering parenteral solutions with conventional equipment and without requiring any special training for such personnel.

Another object of the invention is to provide automatic parenteral infusion equipment of the character described which is fully self contained and portable to facilitate both storage and simplicity of use. Both disposable and reusable adaptations of the equipment may be utilized under varying circumstances.

An additional object of the invention is to provide safe and convenient parenteral equipment of the character described being portable and having features particularly suitable for ambulatory patients. Thus, a user may actually carry on the body equipment embodying this invention to deliver parenteral medication over an extended period of time.

Other and further objects of the invention, together with the features of novelty appurtenant thereto, will appear in the course of the following description of the drawings.

DESCRIPTION OF THE DRAWINGS

In the accompanying drawings which form a part of the specification and are to be read in conjunction therewith, and in which like reference numerals are employed to indicate like parts in the various views.

Figures 1, 2, 3, 4:
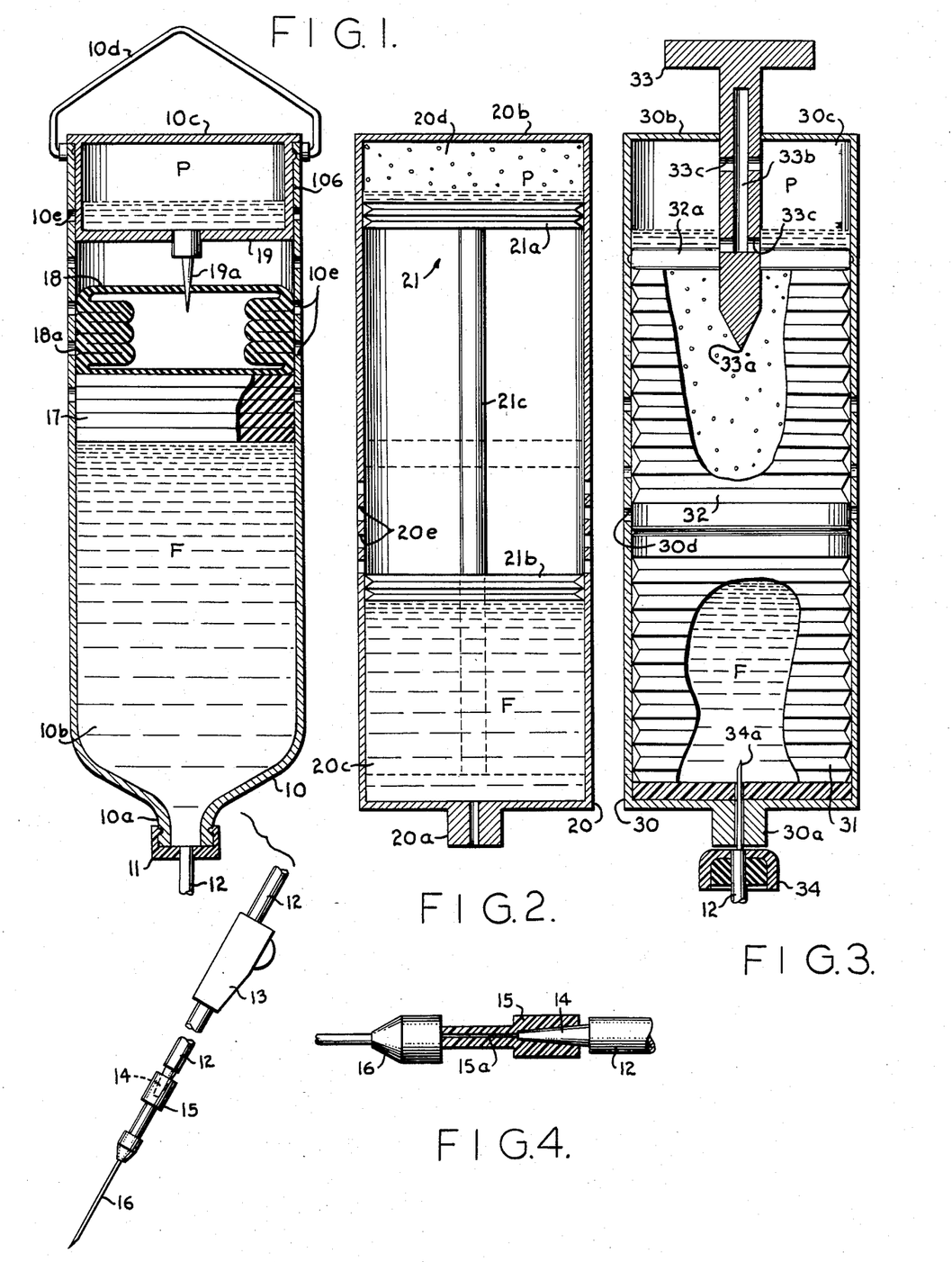
FIG. 1 is a sectional, side elevational view of automatic infusion apparatus illustrating a first embodiment of the invention with portions of the delivery tube broken but indicating continuous length.
FIG. 2 is a sectional, side elevational view of parenteral infusion apparatus illustrating a second embodiment of the invention.
FIG. 3 is a sectional, side elevational view of automatic infusion apparatus illustrating a third embodiment of the invention.
FIG. 4 is an enlarged fragmentary view, partly in section, illustrating the flow regulating fluid delivery mechanism.

Referring to the drawings in more detail, attention is first directed to FIG. 1. The automatic parenteral infusion apparatus includes a cylindrical container shell 10 constructed of a rigid, and preferably, translucent material. The shell 10 is necked down at the lower end 10a thereof and capped with a tubing connector cap 11. Parenteral liquid delivery tubing 12 sealingly penetrates connector cap 11 to communicate with the interior of the container 10. The tubing 12 may be of any suitable length as indicated by the discontinuous lines in FIG. 1 and is equipped with an on/off flow control valve 13. The terminal end of the tubing 12 is fitted with a tapered hollow nozzle 14. As best shown in FIG. 4, the nozzle 14 is positioned within the socket of a flow regulating member 15 having a preselectedly sized orifice 15a therethrough. Removably fitted to the outer end of the flow regulating member 15 is a hypodermic needle 16 to penetrate a patient's body for the delivery of parenteral fluid.

Within the shell 10 is formed a chamber for containing the parenteral fluid designated by the letter F. The chamber 10b containing fluid F is defined by the interior wall surfaces of shell 10 extending from the necked down portion 10a sealed with cap 11 to a movable plug 17 which sealingly engages the interior cylindrical wall of the shell 10. Thus, the plug 17 bears against the upper surface of the fluid F in the equipment as oriented in FIG. 1. Surmounting the plug 17 is an expandable gas bladder 18 having accordion-like pleats 18a forming the cylindrical side surface thereof to permit expansion of the bladder 18 through the length of the shell 10. Contained within the upper end of the shell 10 is a replaceable pressure source cannister 19. The cannister 19 has cylindrical side walls with an outside diameter slightly less than the inside diameter of the shell 10 to define an annulus 10b therebetween. The lower end wall of the cannister 19 is fitted with a hollow needle member 19a adapted to sealingly penetrate the gas bladder 18. The upper end of the cannister 19 is substantially the same diameter as the outside diameter of the shell 10 to overlie the upper edge thereof to properly seat the cannister 19 in the end of the shell 10. The cannister 19 is held in place by a removable cap 10c secured to the shell 10 by threads, a compression gasket, or a similar connection to enable the cap 10c to be removably locked in place on the shell 10.

The cap 10b may be equipped with a hanger wire 10d for suspending the apparatus as shown in FIG. 1. Alternatively, it should be understood that it is not necessary that the equipment be vertically oriented as shown in FIG. 1. Indeed, it may be oriented in virtually any position since delivery of the fluid F to the patient does not rely upon gravity flow.

Between the upper end of the shell 10 and the movable plug 17 are a plurality of openings 10e which provide atmospheric communication with the interior of the container shell 10. The uppermost such opening 10e is positioned adjacent the annulus 10b. The purpose of such openings will be understood shortly.

A pressuring fluid P is contained within the pressure source cannister 19. Preferably, the pressurizing fluid P is a liquid which has a boiling point at atmospheric pressure below room temperature (i.e., below 70° F.), and preferably well below normal ambient temperatures. For example, ethyl chloride having a boiling point at 54° F., at ambient pressure may be selected as pressurizing fluid P. Those skilled in the art will of course recognize that other fluids, such as certain fluorohydrocarbon refrigerants, may also be used as the pressurizing fluid P.

So constructed and assembled, the pressurizing fluid P within cannister 19 communicates through the needle member 19a to the expandable bladder 18 to exert a pressure therein substantially equal to the vapor pressure of fluid P at ambient conditions. The bladder 18 expands to fill the space between the lower surface of the cannister 19 and the upper surface of the movable plug 17. Further expansion of the bladder 18, forces the plug 17 to pressurize the parenteral fluid F which is delivered through the tubing 12 and the flow regulating member 15 to the patient via the hypodermic needle 16. Flow is thus regulated, in accordance with the recognized principles of fluid mechanics, by the substantially constant pressure source of the expandable bladder 18 and the orifice size 15a of the flow regulating device 15.

In the event of rupture or leakage from the cannister 19 or the bladder 18, the pressure fluid P is safely vented to the atmosphere through openings 10e.

Referring to FIG. 2 of the drawings, alternative features of the invention are illustrated. The parenteral liquid container in the form of a rigid, cylindrical shell 20 having a neck 20a on one end thereof with a fluid passageway communicating with the interior of the container. The upper end of the shell 20 is sealed by an end plate 20b. Interiorly of the container is a chamber 20c for the parenteral fluid F which is separated from the chamber 20d pressure fluid P by a spool piece 21. The spool piece 21 is formed by upper and lower movable plugs 21a and b sealingly engaged with the interior cylinder wall of the shell 20 and centrally interconnected by an axial rod 21c. Intermediate the fluid chamber 20c and the pressure source chamber 20d, the shell 20 is provided with a plurality of openings 20e therein communicating with the atmosphere.

In operation, constant pressure supplied by the pressure fluid P is transmitted through the spool piece 21 to the fluid F which is delivered through tubing (not shown) of the character as previously described until the fluid F is fully discharged. The latter condition is illustrated as a broken line view of the spool piece 21 in FIG. 2.

In the event of defect or leakage of pressure around the upper sealing plug 21a, the pressure fluid P will be vented to the atmosphere through the openings 20e in the shell wall to prevent embolism or introduction of toxics to the patient.

Referring to FIG. 3 of the drawings, further modifications of the invention are illustrated in a third embodiment. The container is formed of a rigid, cylindrical shell 30 having a neck 30a with a central opening therethrough. Interiorly of the chamber is a collapsible bag 31 charged with parenteral fluid F. An expandable bladder 32 surmounts the bag 31. The bladder 32 has accordion-like pleats forming the cylindrical side thereof to permit expansion of the bladder 32. The upper circular end wall 32a of the bladder 32 is immovably secured to the interior wall of the shell 30. Thus, defined between the bladder wall 32a and the upper end wall 30b of the shell 30 is a pressure source chamber 30c charged with a pressurizing fluid P. Received within the end wall 30b of the shell 30 is a pressure activating member 33 having a sharpened end 33a which penetrates in a sealing manner the upper end wall 32a of the bladder 32. The pressure actuating member 33 includes an interior bore 33b with spaced radial openings 33c therefrom. When the actuating member 33 is fully depressed the uppermost openings 33c are positioned within pressure chamber 30c and the lowermost set of openings 33c are positioned interiorly of the bladder 32 whereby communication is thus established through bore 33b between the pressure chamber 30c and the interior of the gas bladder 32.

In operation, the actuating plunger 33 is fully depressed to pressurize at a substantially constant pressure the bladder 32. Delivery tubing 12 is received by a fitting 34 having a hollow needle 34a received through the shell neck 30a to sealingly penetrate the bag 31. Expansion of the gas bladder 32 thus causes fluid F to be delivered at a constant rate to the patient through delivery equipment of the character as previously described.

Between the upper end of the bag 31 when fully charged with fluid F and the upper immovable wall of the bladder 32, the shell 30 is provided with a plurality of openings 30d therein communicating with the atmosphere. In the event of a pressure leak or rupture of the gas bladder 32, the pressure fluid will be vented to the atmosphere through the openings 30d in the shell wall to insure the patient's safety.

The embodiments of the invention so described with reference to the embodiments of FIGS. 1–3 thus contemplate disposable and portable infusion equipment. Depending of course on the amount of parenteral fluid to be delivered to the patient, the equipment may be so sized as to be conveniently secured to the body of an ambulatory patient.

Attention is now directed to the fourth embodiment of the invention which contemplates larger and rechargeable equipment which is portable yet, due to its capacity, is not designed to be secured to the patient's body. Reference is made to FIGS. 5–9.

A flexible bag 40 contains a volume of parenteral fluid F to be infused into the patient's body. The bag 40 has an outlet 40a and a length of tubing 42 connected to the bag outlet. As generally indicated at 43, a hypodermic needle is connected to the free end of the tubing for insertion into the patient's body for the flow of fluid F from bag 40 to the patient. An adjustable valve or flow regulator 44 is provided along tube 42 for controlling the rate of flow of fluid F through the tube to the patient. Alternatively, a fixed regulating device such as member 15 shown in FIG. 4 may be utilized.

Figure 7:
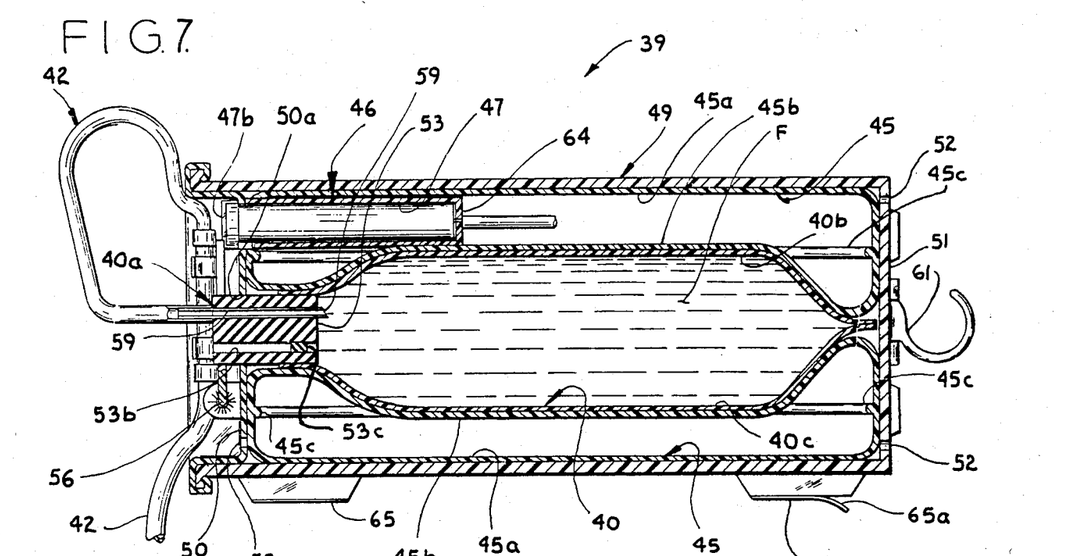
FIG. 7 is a longitudinal side sectional view of the infusion apparatus shown in FIG. 5.
Figure 8:
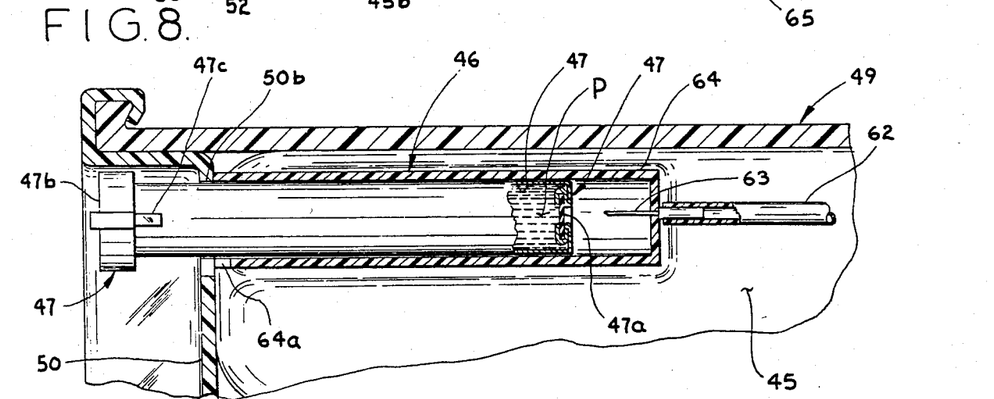
FIG. 8 is an enlarged fragmentary view of a portion of the apparatus shown in FIG. 7 illustrating means for effecting pressurization of the liquid in the parenteral bag with the pressurizing means being illustrated in a ready to use configuration.
Figure 9:
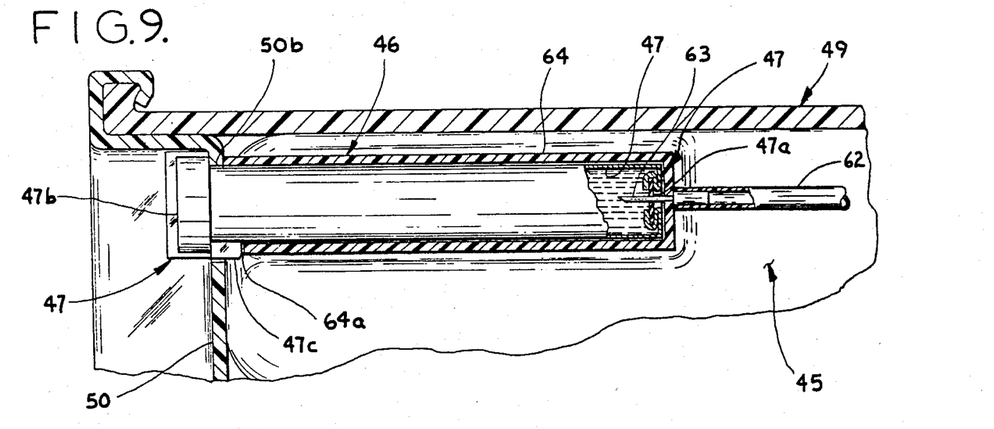
FIG. 9 is a view similar to that of FIG. 8, but showing the pressurizing means shifted to an activated configuration.

A pressurizable, annular bladder 45 surrounds bag 40 and at least one end of the bladder 45 is open for reception of the bag 40. As indicated at 46, selectively actuable means is provided for pressurizing the bladder and for thus effecting pressurization of fluid F in the bag. In FIGS. 7–9, this pressurization means is shown to comprise a closed tank or container 47 having a volume of pressure fluid P therein.

Actuator means 46 further comprises selectively operable means, as generally indicated at 48, for providing communication between container 47 and bladder 45 so as to permit the flow of pressurizing fluid P from the container to the bladder for pressurization of the latter and the liquid F within bag 40 and to maintain the liquid in the bag under substantially constant pressure as the liquid F drains from the bag.

More specifically, apparatus 39 includes a nonexpansible housing 49, preferably constructed of a rigid, transparent material. The housing 49 is generally rectangular in cross section having a removable end closure 50 at one end thereof constituting its front end and a fixed closure 51 at the other end of the enclosure (see FIG. 7). With removable closure 50 removed, bladder 45 with bag 40 therein is insertable in the housing 49. Closures 50 and 51 have apertures 52 therein to vent the inside of housing 49 to the atmosphere. With closure 50 snapped in place on housing 49, it will be noted that the interior of the housing is at atmospheric pressure.

Bag 40 is a flexible bag having walls 40b and 40c (see FIG. 7) sealed together, such as by heat-sealing, substantially around the periphery of the bag. Bag outlet 40a is provided at one end of the bag, this outlet being shown to comprise a stopper 53 sealingly secured to and extending out from the end of the bag. Stopper 53 has a pair of ports 53a and b therein into which a hollow lance may be inserted (as will be hereinafter explained) for connection tube 42 to the bag and for the injection of various medicants into the bag by means of a hypodermic needle or the like. Each port 53a & b has a puncturable seal 53c.

Bladder 45 is made of flexible material, such as a suitable plastic film, and is shown to have an outer wall 45a and an inner wall 45b joined together a seal 45c (see FIG. 7). Thus, an annular bladder is defined having at least one open end which is of sufficient size to permit bag 40 filled with liquid F to be inserted within the bladder. Upon pressurizing bladder 45, its outer wall 45a expands to bear against the inside surface of housing 49. As previously stated, housing 49 is preferably of rigid construction so that it serves to contain the outward expansion of the bladder 45 and to thus force the bladder to compress bag 40 as the bladder is pressurized.

As shown in FIG. 7, with a filled bag 40 positioned within bladder 45, with the bladder and bag installed in housing 49, and with closure 50 in place on the housing, stopper 53 extends from the bag 40, and passes through an aperture 50a in closure 50.

Figure 5:
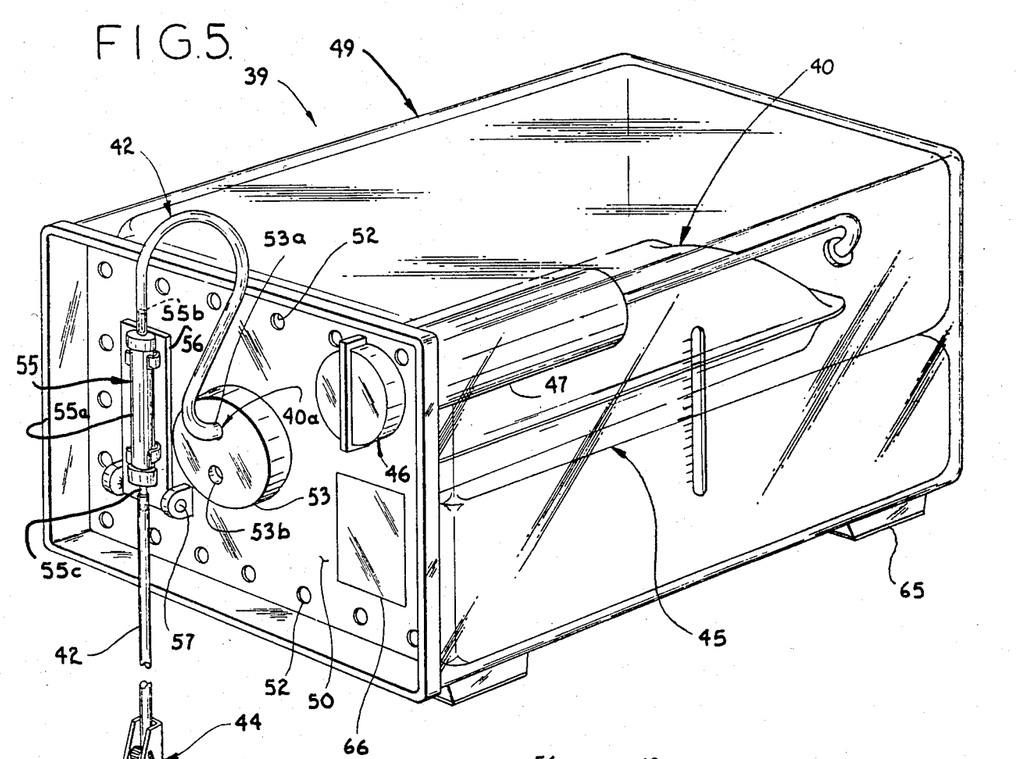
FIG. 5 is a perspective view of automatic parenteral infusion apparatus illustrating a fourth embodiment of the invention.
Figure 6:
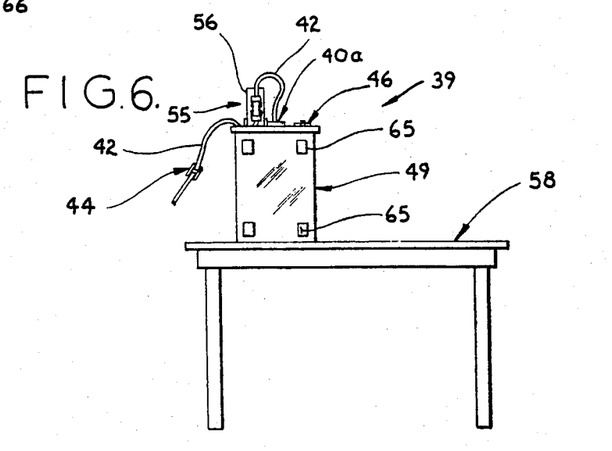
FIG. 6 is a side elevational view of the automatic parenteral infusion apparatus in a typical operational setting.

As indicated generally at 55 in FIG. 5, a drip chamber is provided on closure 50. This drip chamber comprises a transparent cylinder 55a of substantially larger diameter than tube 42 and has an inlet nipple 55b at one end thereof and an outlet nipple 55c at its other end. The inlet nipple 55b extends into the cylinder 55a so that with the drip chamber 55 in its normal operating position, the chamber 55 is substantially vertical with the inlet nipple 55b above the outlet nipple 55c, and with liquid F entering the drip chamber via the inlet nipple, drops of substantially uniform size of liquid are formed at the lower end of the inlet nipple within cylinder 55a at a rate corresponding to the flow rate of liquid from bag 40. By adjusting valve 44 and by counting the number of drops in a predetermined length of time, the flow rate may be determined and may be adjusted within a limited range. As best shown in FIGS. 5 and 6, the drip chamber is carried by a bracket 56 hingedly secured to closure 50 by hinges 57. Bracket 56 is swingable from a first position (as shown in FIG. 5) in which it is generally parallel to closure 50 and a second position (as shown in FIG. 6) in which it is generally perpendicular to closure 50. As will be hereinafter explained, apparatus 39 is operable either when lying in a horizontal position or when standing vertically and facing upwardly. When lying horizontally with bracket 56 in its first position, it will be noted that inlet nipple 55b of the drip chamber is at the top of the drip chamber and when standing upright on a table 58 (FIG. 6) with bracket 56 in its second position the inlet nipple is again at the top of the drip chamber. Tubing 42 includes a first length attached to inlet nipple 55b and a second length attached to the outlet nipple 55c. The free end of the first length of tubing 42 carries a hollow lance 59 which is insertable in a port 53a or b or stopper 53 to puncture the seal 53c therein and to permit the outflow of liquid F. Tubing 42 has valve means 44 located therealong and has needle 43 at its free end. A puncturable port fitting 60 may be provided in tubing 42 into which medication may be injected via a hypodermic needle for infusion into the patient with liquid F.

In addition to being operable in the abovementioned horizontal and standing position, the apparatus 39 is also operable by hanging housing 49 with end closure 51 facing downwardly. This permits operation of the apparatus in the event the pressurization system 46 is inoperable. A hook 61 (see FIG. 7) is provided on end wall 51 for hanging housing 49 from an IV pole in the same manner as a conventional IV bag. Hook 61 is preferably hingedly connected to end wall 51 and may be folded flat. With the housing hanging from hook 61, bag opening 40a is at the bottom of the bag. Drip monitor 55 may be unclipped from bracket 56 and allowed to hang in a vertical orientation.

Pressure means 46 includes a length of tubing 62 sealingly secured to and in communication with bladder 45 and having a hollow lance 63 at its other end. Lance 63 is held in fixed relation to housing 49 at one end of a tubular guide 64. Guide 64 is secured to the inside of closure 50 and extends along one corner of housing 49. It will be understood that bladder 45, when pressurized, bears against the outside of the guide 64. Container 47 has a puncturable seal 47a at its end adjacent lance 63 and is axially movable in guide 64 between a first position (FIG. 8) in which the seal is spaced from the tip of lance 63 and a second or actuated position (FIG. 9) in which the lance has punctured the seal to release fluid P from container 47 for pressurization of bladder 45 with consequent pressurization of liquid F in bag 40.

Container 47 has an actuating handle 47b which extends exteriorly of end closure 50 through an aperture 50b in closure 50 for permitting manual movement of container 47 relative to lance 63 between its first and second positions. As best shown in FIGS. 8 and 9, container 47 is an elongate cylinder and it has a lug 47c thereon extending axially on its outer surface. Guide 64 has an axial slot 64a adapted for reception of lug 47c on container 47 when the container is rotated from a locked position in which the lug and the slot are out of register and an actuation position in which the lug and slot are aligned with one another. With handle 47b in its safe position (FIG. 8), idadvertent puncturing of seal 47a on container 47 and accidental pressurization of bladder 45 is prevented.

As best shown in FIG. 5, housing 49 has a viewing window 49a in one of its sides and a volume indicating scale 49b is provided on the housing adjacent the window. Preferably, bladder 45 and bag 40 are of transparent plastic film or the like so that the quantity of liquid F remaining in bag 40 may readily be estimated by observing the bag through window 49a and comparing the volume remaining in the bag with scale 49b.

On the bottom of housing 49, strips of pressure sensitive tape or the like, as indicated at 65, having a removable outer cover or backing 65a are provided. Upon use of the apparatus of this invention, covers 65a may be peeled away and the housing adhered to a supporting surface, such as the floor of an ambulance or a bedside table, to prevent movement of the apparatus relative to the patient. Also, a label 66 (see FIG. 5) may be adhered to closure 50 listing pertinent information regarding liquid F and administration of the liquid to the patient.

As has been heretofore pointed out, bladder 45 and bag 40, when inserted in housing 49 with closure 50 in place, are open to the atmosphere. Thus, in the event of a rupture or a leak of pressure container 47 prior to use, the pressurizing fluid P is simply vented to the atmosphere without effecting pressurization of bag 40. In the event of a leak in bag 40, liquid F is permitted to drain from the bag and from the enclosure. Since the pressurizing fluid is separated from bag 40 by inner wall 45b of bladder 45 and does not directly act against bag 40, none of the pressurizing fluid will enter bag 40 in the event of a leak in the bag. Likewise, in the event of a rupture of bladder 45 during use, the pressurizing fluid P is harmlessly vented to atmosphere through vents 52. This significantly reduces the danger of gas embolism or chemical toxicity to the patient.

By using a fluid P, such as ethyl chloride, having a boiling point below room temperature, bladder 45 is readily pressurized to a desired operating pressure at which liquid F is forced from bag 40 at a predetermined pressure (i.e., the vapor pressure of fluid P). By adjusting valve 44, the flow rate of liquid F to the patient may readily be controlled. As liquid F drains from bag 40, fluid P will automatically compensate for the increase in volume of bladder 45 to maintain a relatively constant pressure on bag 40. Thus, the pressure with which liquid F is exhausted is not dependent on the elevation of the equipment above the patient. It can therefore be seen that the infusion apparatus of the present invention may readily be used in battlefields, ambulances, helicopters and hospitals without the requirement of elevating the equipment.

Figure 10:
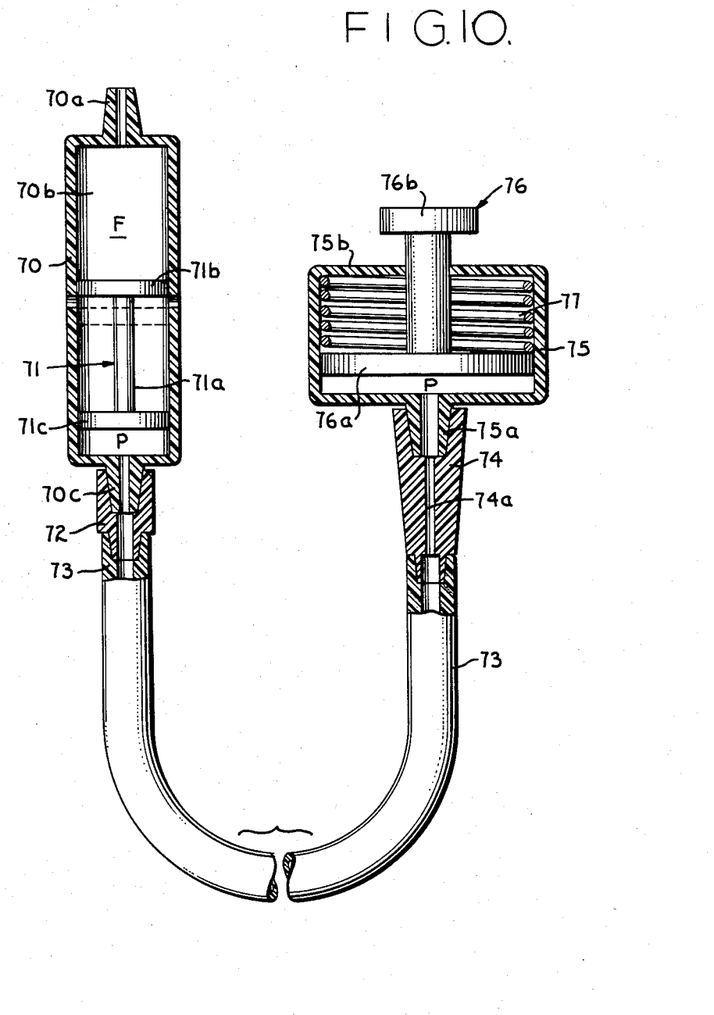
FIG. 10. is a sectional, side elevational view of automatic infusion apparatus illustrating a fifth embodiment of the invention.

Attention is now directed to FIG. 10 illustrating a final embodiment of the invention. As contemplated in the embodiments of FIGS. 1-3, the FIG. 10 embodiment includes a disposable infusion unit along with a reusable pressure unit, all of which may be conveniently carried on the body of an ambulatory patient.

The disposable infusion syringe is formed of a rigid, cylindrical shell 70 having a neck 70a on one end thereof with a central opening. A suitable fitting and delivery tubing (not shown) may be connected to the neck 70a as will be understood with reference to the prior embodiments. Bearing against infusion liquid contained within the infusion chamber 70b of the shell 70 is a spool piece plunger 71 formed from a central rod 71a having movable plugs 71b & c on each end thereof sealingly engaged with the interior cylindrical wall of the shell 70. Vent openings are provided in the shell to be positioned between the movable plugs 71b & c irrespective of the position within the shell 70 of the spool piece 71.

The end of the shell 70 opposite the neck portion 70a connected to the infusion liquid delivery tubing likewise includes a neck portion 70c having a central opening therethrough. Connected to the neck portion 70c is a flow fitting 72 equipped with a length of tubing 73. The opposite end of the tubing 73 is fitted with a flow regulating device 74 having an orifice 74a therethrough. The regulating device 74 is removably connected to a mechanical pressure source unit.

The pressure source includes a cylindrical housing 75 having a neck 75a at one end thereof with a central opening therethrough on which is received the flow regulator 74. The housing 75 contains a movable plunger 76 having a plug member 76a sealingly, yet movably, engaged with the interior surface of the housing 75 with a handle member 76b which extends outwardly from the closed end 75b the housing 75. Captured within the housing 75 and encircling the plunger 76 is a compression spring 77 which bears against the back of the plunger plug 76a and urges it towards the necked end 75a of the housing 75.

A fluid passageway is thus defined between the forward face of the plunger plug 76a and the rear plug 71c of the spool piece 71 in the shell 70 which holds the infusion liquid F. This fluid passageway is filled with an incompressible fluid P. Further, the interior diameter of the pressure force housing 75 is larger than the interior diameter of the infusion liquid shell 70.

In operation, therefore, the pressure source forcing the infusion liquid F to the patient is supplied by the spring 77 urging against the incompressible fluid P which transmits this force to the spool piece 71 of the infusion syringe. Because the diameter of the pressure plunger 76a is larger than the diameter of the spool piece 71 bearing against the infusion liquid F, a small lineal movement of the plunger 76 under the influence of the compression spring 77 will result in a larger lineal movement of the spool piece 71 to discharge infusion liquid F from the syringe. The rate of infusion is controlled by the flow regulating device 74 having an appropriately sized restriction orifice 74a. The flow regulating device 74 may be positioned either on one end or within the hose communicating between the pressure source and the infusion syringe or on one end or between the hose used to deliver the infusion liquid to the patient.

It should again be noted with reference to this final embodiment of the invention that the pressure transmitting fluid P, in this case an incompressible liquid, does not directly engage the infusion liquid F itself. Thus, as a safety feature, if the incompressible pressure fluid P should happen to leak from around the rear plug 71c of the spool piece 71, it will be harmlessly leaked from the infusion syringe 70 without presenting any toxicity hazard by introduction to the patient's body.

From the foregoing it will be seen that this invention is one well adapted to attain all the ends and object hereinabove set forth together with the other advantages which are obvious and which are inherent to the structure.

It will be understood that certain features and subcombinations are of utility and may be employed without reference to other features and subcombinations. This is contemplated by and within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, I claim:

1. Automatic parenteral infusion apparatus to deliver infusion liquid to a patient at a substantially constant rate and pressure, said apparatus comprising:
   a rigid shell having a hollow interior;
   means within said shell defining an infusion liquid chamber being reducible in volume and adapted for containing infusion liquid;
   means including a pressure source chamber spaced apart from said infusion liquid chamber to contain a pressure fluid and adapted to supply a substantially constant pressure within an expandable volume;
   pressure transmission means interposed within said shell between said infusion liquid chamber means and said pressure source chamber means to transmit a substantially constant pressure from said pressure source chamber to said infusion liquid chamber;
   delivery means connected to said infusion liquid chamber means to delivery infusion liquid at a controlled and constant rate of flow; and
   vent means in said shell intermediate said infusion liquid chamber means and said pressure source chamber means to provide constant atmospheric communication with the interior of said shell at all times throughout delivery of infusion liquid to a patient whereby any pressure leakage from said pressure source chamber means is safely discharged to the atmosphere.

2. The parenteral infusion apparatus as in claim 1, said infusion liquid chamber means including a movable plug member received interiorly of said shell in sealing engagement therewith for containing infusion liquid in one end of said shell and sealingly movable on the interior wall of said shell with the reduction in volume of said infusion liquid as same is discharged from said chamber means.

3. The parenteral infusion apparatus as in claim 1, said pressure transmission means comprising a spool member having first and second plug members disposed within said shell and being interconnected by a rigid support member, said first plug movable within said shell in sealing engagement therewith adjacent said pressure source chamber means and said second plug member movable within said shell in sealing engagement therewith adjacent said infusion liquid chamber means.

4. The parenteral infusion apparatus as in claim 1, said pressure source chamber means including a fluid passageway of fixed volume filled with incompressible fluid acting upon said pressure transmission means and mechanical force means acting upon said fluid passageway.

5. Parenteral infusion apparatus as in claim 1, said pressure fluid comprising a liquid having a normal boiling point below ambient temperature whereby the substantially constant pressure corresponds approximately to the vapor pressure of said liquid at ambient conditions.

6. Automatic parenteral infusion apparatus to deliver infusion liquid to a patient at a substantially constant rate and pressure, said apparatus comprising:
   a rigid shell having a hollow interior;
   means within said shell defining an infusion liquid chamber being reducible in volume and adapted for containing infusion liquid;
   means including a pressure source chamber spaced apart from said infusion liquid chamber to contain a pressure fluid and adapted to supply a substantially constant pressure within an expandable volume;
   pressure transmission means interposed within said shell between said infusion liquid chamber means and said pressure source chamber means to transmit a substantially constant pressure from said pressure source chamber to said infusion liquid chamber;
   delivery means connected to said infusion liquid chamber means to delivery infusion liquid at a controlled and constant rate of flow, said delivery means including a flow regulating valve to variably supply a constant rate of flow of infusion liquid at a substantially constant pressure; and
   vent means in said shell intermediate said infusion liquid chamber means and said pressure source chamber means to provide constant atmospheric communication with the interior of said shell at all times throughout delivery of infusion liquid to a patient whereby any pressure leakage from said pressure source chamber means is safely discharged to the atmosphere.

7. Automatic parenteral infusion apparatus to deliver infusion liquid to a patient at a substantially constant rate and pressure, said apparatus comprising:
   a rigid shell having a hollow interior;
   means within said shell defining an infusion liquid chamber being reducible in volume and adapted for containing infusion liquid;
   means including a pressure source chamber spaced apart from said infusion liquid chamber to contain a pressure fluid and adapted to supply a substantially constant pressure within an expandable volume;
   pressure transmission means interposed within said shell between said infusion liquid chamber means and said pressure source chamber means to transmit a substantially constant pressure from said pressure source chamber to said infusion liquid chamber;
   delivery means connected to said infusion liquid chamber means to delivery infusion liquid at a controlled and constant rate of flow, said delivery means including a flow regulating member having a preselectedly sized orifice therethrough to supply a constant flow of infusion liquid at a substantially constant pressure; and
   vent means in said shell intermediate said infusion liquid chamber means and said pressure source chamber means to provide constant atmospheric communication with the interior of said shell at all times throughout delivery of infusion liquid to a patient whereby any pressure leakage from said pressure source chamber means is safely discharged to the atmosphere.

* * * * *